United States Patent [19]

Staver

[11] Patent Number: 4,469,105

[45] Date of Patent: Sep. 4, 1984

[54] MEDICAL ELECTRODE APPARATUS AND KIT OF COMPONENTS THEREFOR

[75] Inventor: Peter J. Staver, Lincoln Park, Mich.

[73] Assignee: Clinton Meyering, Southgate, Mich.

[21] Appl. No.: 274,825

[22] Filed: Jun. 18, 1981

[51] Int. Cl.³ ............................................. A61B 5/04
[52] U.S. Cl. ................................................... 128/643
[58] Field of Search ........................ 128/643, 802, 803

[56] References Cited

U.S. PATENT DOCUMENTS

| | | | |
|---|---|---|---|
| 2,983,273 | 5/1961 | Howell | 128/643 |
| 3,490,442 | 1/1970 | Streu | 128/643 |
| 3,862,627 | 1/1975 | Hans, Sr. | 128/643 |
| 3,976,055 | 8/1976 | Monter et al. | 128/643 |
| 4,369,793 | 1/1983 | Staver et al. | 128/643 |

FOREIGN PATENT DOCUMENTS 449729  4/1975  U.S.S.R. ............................. 128/643

Primary Examiner—Lee S. Cohen
Attorney, Agent, or Firm—Irving M. Weiner; Pamela S. Burt; Anthony L. Cupoli

[57] ABSTRACT

A medical electrode apparatus and a kit of components therefor, for use on the skin of a patient in conjunction with an external medical instrument such as an EKG machine. The apparatus includes a resilient bulb member for creating a partial vacuum in a vacuum bell to which it is selectively connected. The vacuum bell is formed with a lower outer concavity surrounding an inner chamber thereof so as to receive therein an electrically-conductive gel material for contact with the patient's skin. Alternatively, the bell may be formed with an annular rim member formed of a closed-cell electrically-conductive sponge material. The vacuum bell is also provided with a connector member for securing therein an electrode terminal of an external medical instrument.

9 Claims, 7 Drawing Figures

MEDICAL ELECTRODE APPARATUS AND KIT OF COMPONENTS THEREFOR

BACKGROUND OF THE INVENTION

1. Field of the Invention

The present invention relates generally to a medical electrode apparatus, and a kit of components therefor, for use on the skin of a subject, the apparatus being used in conjunction with an external medical instrument such as, for example, an electrocardiograph machine.

More particularly, the invention relates to a medical instrumentation electrode apparatus employing a vacuum effect created by a resilient bulb member communicating with a rigid and electrically-conductive vacuum bell member so as to hold the lower open end of the vacuum bell in contact with the subject's skin, as well as a medical instrumentation electrode kit including various component parts which may be readily assembled to form the apparatus in accordance with the invention.

2. Description of Relevant Art

In various medical applications such as electrocardiography, electrical wiring is connected between the surface of a human body and an external medical instrument, such as an electrocardiograph (EKG) machine, so as to measure and record medical data such as electrical waveforms emitted by the human heart. Heretofore, various types of apparatus have been employed for connecting the wiring with the body surface. Common techniques include the use of flat metallic plates which are taped in position against the skin, or the use of an electrically conductive suction cup. Both such techniques require the application of a coating of conductive jelly to the skin surface to ensure proper electrical contact.

Illustrative of known attempts to overcome the difficulties encountered in attaching electrical wires to the skin surface of either a human or other mammal are: the "SUCTION ELECTRODE" disclosed in U.S. Pat. No. 2,580,628 issued in 1952 to Welsh; the "MASSAGING EQUIPMENT" disclosed in U.S. Pat. No. 2,619,278 issued in 1952 to Ackerman; the "SPRING-LOADED SUCTION CUP-TYPE BIOMEDICAL INSTRUMENTATION ELECTRODE" disclosed in U.S. Pat. No. 3,534,733 issued in 1970 to Phipps; the "ELECTRIC CONTACTOR WITH VENTURI-SUCTION MEANS FOR ORGANIC TISSUE" disclosed in U.S. Pat. No. 3,640,270 issued in 1972 to Hoffmann; the "SUCTION ELECTRODE" disclosed in U.S. Pat. No. 3,783,865 issued in 1974 to Ricketts; the "ELECTRODE AND CONDUCTOR THEREFOR" disclosed in U.S. Pat. No. 3,976,055 issued in 1976 to Monter et al; and the "THERAPEUTICAL/DIAGNOSTIC SUCTION ELECTRODE" disclosed in German Auslegeschrift No. 2,208,653 dated Apr. 5, 1973 in the name of Heyne.

The aforesaid various known devices have generally proven deficient in providing ease of use, structural simplicity, adaptability for use with various types of external medical apparatus, and various other desired features.

The present invention provides a medical electrode apparatus and kit therefor which effectively overcomes the various problems associated with prior known devices, and which effectively attains each of the aforesaid desired features. The apparatus in accordance with the present invention may be employed as a Vector Lead electrode which is adaptable to virtually any currently employed conventional EKG machine, eliminates the need for any messy application of conductive gel to the subject's skin, and is generally convenient to use.

SUMMARY OF THE INVENTION

In accordance with a first embodiment, the present invention provides a medical instrumentation electrode apparatus including a substantially rigid and hollow vacuum bell fabricated of a first substantially rigid electrically-conductive material, and first means for creating a partial vacuum in the vacuum bell. The vacuum bell is provided with an upper stem portion formed integrally with the vacuum bell so as to extend upwardly therefrom, the stem portion being fabricated of the first electrically-conductive material, and including an upper portion for selective interconnection with the first means. An air communication passage is defined between the vacuum bell and the first means and is integrally formed in the stem portion. Second means are provided for selectively operably connecting the stem portion to an external medical instrument, and an annular member is secured co-extensively around the periphery of the lower open end of the vacuum bell, the annular member being fabricated of a second substantially resilient electrically-conductive material. Preferably, the first means comprises a resilient bulb member having a neck which is closely received on the upper portion of the stem of the vacuum bell, and the second means comprises a female-conductor type connector operably disposed in an aperture formed in the stem portion of the vacuum bell. The first material desirably comprises an electrically-conductive rigid plastic material and the second material desirably comprises an electrically-conductive closed-cell sponge material, such as a non-skinned closed-cell neoprene material.

In accordance with a second preferred embodiment of the present invention, there is provided a medical instrumentation electrode apparatus including a substantially rigid vacuum bell fabricated of a substantially rigid electrically-conductive material, the vacuum bell having an inner chamber formed therein. First means are provided for creating a partial vacuum in the inner chamber of the vacuum bell, and second means are provided for selectively operably connecting the vacuum bell to an external medical instrument. Third means are provided for operably connecting the first means with the vacuum bell such that the first means communicates with the inner chamber of the vacuum bell. The inner chamber of the vacuum bell includes a lower open end portion defined by a lower peripheral wall portion of the vacuum bell, the lower wall portion having a substantially annular-shaped concavity formed therein so as to define an outer concavity, surrounding the inner chamber, for receiving therein a mass of electrically-conductive material. Preferably, the first means comprises a resilient bulb member having a neck; the second means comprises a substantially tubular connector extending from an outer surface portion of the vacuum bell and integrally fabricated from the same electrically-conductive material such that the vacuum bell and tubular connector comprise a unitary structure; and the third means comprises an electrically-conductive tubular shaped insert having an upper portion adapted to be closely received in the neck of the bulb and a lower portion adapted to be closely received in an upper through aperture provided in the vacuum bell so as to communicate with the inner chamber thereof. The mass of electrically-conductive material received within the annular-shaped concavity preferably comprises an annular mass of electrically-conductive silver-silver chloride gel.

The present invention also provides a kit of components for forming a medical electrode apparatus in accordance with the second preferred embodiment. Such a kit includes a plurality of the vacuum bells, at least one of the resilient bulb members, the tubular shaped insert, and the tubular connector formed in the vacuum bell for connecting same to an external medical instrument.

It is an object of the invention to provide a medical instrumentation electrode apparatus employing a minimum number of component parts so as to thus facilitate mass production thereof, and which is generally convenient and highly effective in use.

The above and other objects and details of the present invention will become apparent from the following detailed description, when read in conjunction with the accompanying drawings.

DETAILED DESCRIPTION OF THE PREFERRED EMBODIMENTS

Figure 1:
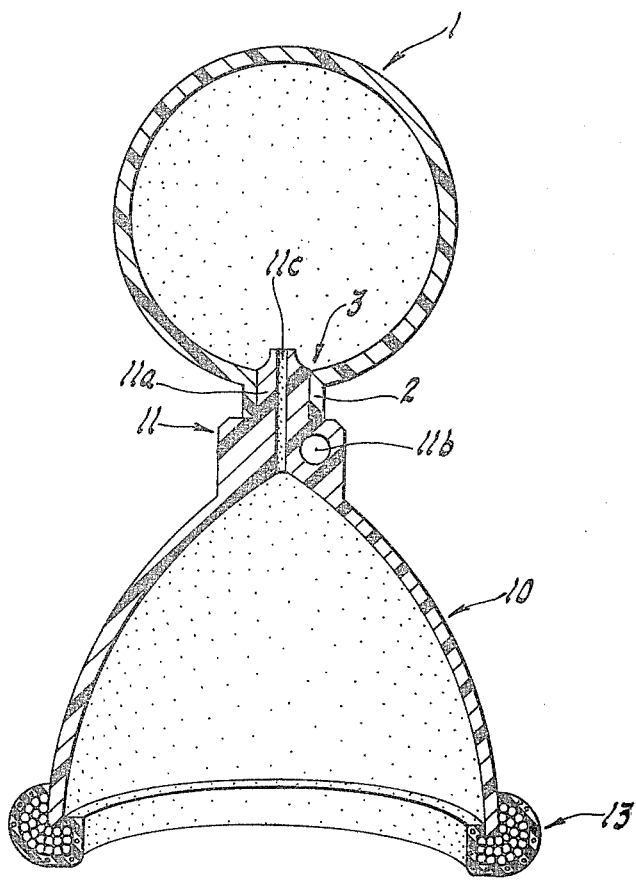
FIG. 1 depicts a sectioned view of a medical electrode apparatus in accordance with a first embodiment of the invention.

With reference to FIG. 1, there is shown a medical instrumentation electrode apparatus in accordance with a first embodiment of the invention. The apparatus includes a resilient bulb member 1, which may be fabricated from a conventional rubber or elastomeric material. Bulb 1 has substantially a suction cup structure, and is of a sufficient size to produce a partial vacuum within the vacuum bell 10, as will be described hereinbelow. The bulb 1 includes an integral neck 2 having a cylindrical opening 3 extending coaxially therethrough so as to permit selective interconnection of bulb 1 with vacuum bell 10, as will be described in detail hereinbelow.

Figure 2:
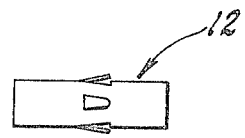
FIG. 2 illustrates a side elevational view of female conductor type connector for use with the apparatus of FIG. 1.

The substantially hollow vacuum bell 10 is fabricated of a substantially rigid electrically-conductive material, such as by injection molding an electrically-conductive plastic which desirably has minimal resistance, such as for example, a polypropylene-base resin known as CAPREZ DPP available from Alloy Polymers of Waldwick, N.J. As shown in FIG. 1, the vacuum bell 10 is integrally formed (i.e., with the aforesaid electrically-conductive material) with an upwardly extending stem portion 11 including a reduced-diameter upper portion 11a which is particularly dimensioned so as to closely receive therearound the neck 2 of bulb 1. The thicker lower portion of stem 11 is formed with an aperture or bore 11b for receiving therein a female-conductor type connector 12 (FIG. 2) of a known construction, which permits selective operable connection of vacuum bell 10 (via stem 11) to an external medical instrument, as will be described hereinbelow. Connector 12 is of the type which is commonly employed, for example, in tube testing devices, and incorporates a friction design for receiving and holding therein the common terminal of an EKG machine, as described hereinbelow.

A substantially straight air communication passage 11c is integrally formed within stem 11 so as to extend from the uppermost end thereof to the lower end thereof, thus defining an air communication passage between bulb 1 and the interior of vacuum bell 10.

With further reference to FIG. 1, the vacuum bell 10 is provided with a lower rim in the form of an annular member 13 which is fabricated of an electrically-conductive closed-cell sponge material, such as a non-skinned closed-cell neoprene sponge material. As shown, the annular member 13 is secured co-extensively around the periphery of the lower open end of vacuum bell 10 so as to contact bell 10 at the inner surface, base and outer surface thereof, and preferably is affixed to bell 10 along the outer surface of bell 10 by suitable adhesive means.

In operation, the apparatus of FIG. 1 is connected with an external medical instrument, such as an EKG machine, by inserting a male electrode terminal of the machine into the female connector 12 positioned within aperture 11b. The bulb 1 is squeezed to deform same and force air through passage 11c into vacuum bell 10, and the bell 10 is then positioned such that annular member 13 contacts the patient's skin. Upon release of the squeezing hold on bulb 1, air will be evacuated from bell 10 through passage 11c to the interior of bulb 1, thus creating a partial vacuum in bell 10. Such evacuation will result in a strong holding of the annular member 13 of bell 10 against the patient's skin, with the electrical path from the EKG electrode terminal being defined through the electrically-conductive stem 11, bell 10, and annular member 13 to the patient's skin. The apparatus is universally adaptable to all types of available EKG machines, and the structure of bell 10 with annular member 13 will ensure effective contact with the patient's skin.

The various component parts of the apparatus as above described may be readily assembled and disassembled for replacement of desired components, e.g., bulb 1 may be removed from vacuum bell 10 and connected with another vacuum bell.

By way of example, the bell 10 may be approximately 2½ centimeters in diameter, while the dome height thereof may be approximately the same.

With reference to FIGS. 3-7, a medical instrumentation electrode apparatus in accordance with a second preferred embodiment of the invention will now be described, with like reference numerals being employed to designate like parts. In this embodiment, the resilient bulb member 1 is substantially the same as bulb member 1 described hereinabove with reference to FIG. 1, including the neck 2 and cylindrical opening 3.

The vacuum bell 14 of the second embodiment is fabricated of the same above-described substantially rigid electrically-conductive material of which vacuum bell 10 is formed, and may be desirably integrally injection molded from the aforesaid CAPREZ DPP material to have substantially the same overall dimensions as bell 10. Vacuum bell 14 is formed with a relatively thick wall (see FIG. 7) so as to define an inner chamber 15 therein. The lower open end portion of bell 14 (and chamber 15) is defined by a lower peripheral wall portion having a substantially annular-shaped concavity 16 formed therein so as to concentrically surround inner chamber 15 of bell 14. The concavity 16 is particularly provided for receiving therein a mass of electrically-conductive material as will be described in detail hereinbelow. The central upper portion of bell 14 is integrally formed with a through aperture 17 which communicates with inner chamber 15 as shown in FIG. 7.

A substantially tubular shaped insert member 18, formed of a rigid material such as metal, is provided for selectively operably interconnecting bulb 1 with bell 14. The insert 18 is formed with a centrally disposed peripheral flange 18a, and the upper portion of insert 18 above flange 18a is adapted to be closely received in neck 2 of bulb 1 such that the upper surface of flange 18a is positioned substantially in abutting relation with the lower end of neck 2. The lower portion of insert 18a is in turn adapted to be closely received in aperture 17 of bell 14 such that the lower surface of flange 18a is positioned against the upper surface of bell 14. Preferably, the upper portion of insert 18 is adhesively or otherwise secured within neck 2 of bulb 1, while the lower portion of insert 18 is selectively slidably insertable and removable from aperture 17, and is retained therein by a substantially airtight friction fit. It will thus be understood that insert 18 permits selective interconnection of bulb 1 with vacuum bell 14 such that bulb 1 communicates with inner chamber 15.

Figure 4:
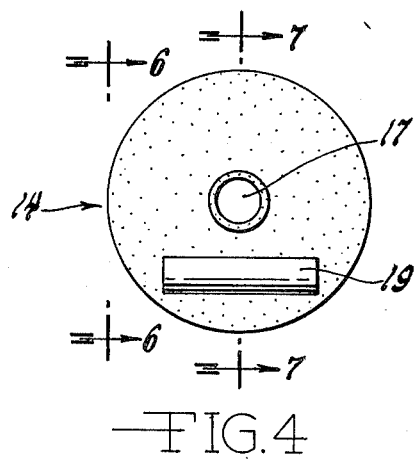
FIG. 4 is a view taken along line 4—4 in FIG. 3.
Figure 5:
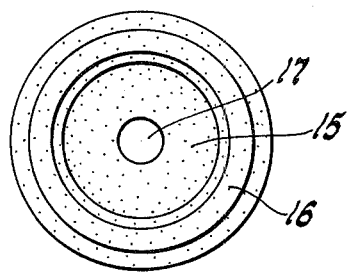
FIG. 5 is a view taken along line 5—5 in FIG. 3.
Figure 6:
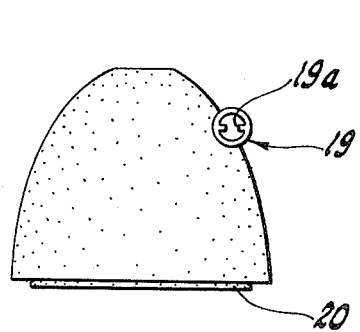
FIG. 6 is a view taken along line 6—6 in FIG. 4.

The vacuum bell 14 is also integrally formed with a substantially tubular-shaped connector member 19 extending integrally from an outer surface portion of vacuum bell 14. The connector 19 is integrally fabricated (i.e., injection molded together with the remainder of bell 14) from the aforesaid electrically-conductive material such that vacuum bell 14 and connector 19 comprise a unitary structure, with connector 19 being positioned substantially centrally as shown in FIG. 4 to provide stability when an EKG machine terminal is secured therein. A pair of inner centrally-disposed friction projections 19a are integrally formed in connector 19 as shown in FIG. 6, so as to permit secure retention of an EKG machine terminal therein as described below.

Figure 7:
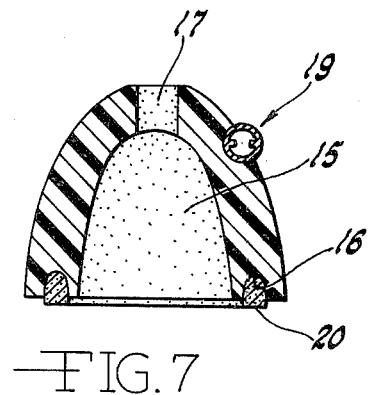
FIG. 7 is a view taken along line 7—7 in FIG. 4.

The annular concavity 16 of bell 14 is adapted to receive therein a mass of electrically-conductive material 20 as shown in FIG. 7. The material 20 preferably comprises a substantially annular-shaped (i.e., toroidal-shaped) mass of a silver-silver chloride compound gel enclosed within a porous gauze material, as available from the 3M Company. Use of such material is particularly advantageous in view of the fact that the normal resistance associated with human skin is approximately 500 ohms, whereas use of the silver-silver chloride gel material against the skin will reduce such resistance to approximately 35 ohms, for which many commom EKG machines are adapted for use. In addition, the substantial moisture content of the gel material facilitates application of the apparatus to a particularly hairy area of skin (e.g., a chest area) by affording a substantially adhesive bond with the skin even in hairy areas.

In operation, the apparatus is connected with an external medical instrument, such as an EKG machine, by inserting a male terminal of the machine into the connector 19 such that it is retained in position by friction projections 19a. The bulb 1 is squeezed to deform same and force air through vacuum bell 14, and the bell 14 is then positioned such that the annular mass of material 20 is in contact with the patient's skin. Upon release of the squeezing hold on bulb 1, air will be evacuated from chamber 15 of bell 14 through insert 18 into the interior of bulb 1, thus creating a partial vacuum in bell 14 and drawing the material 20 into secure holding contact with the patient's skin. The characteristics of material 20 will ensure secure positioning of bell 14 against the patient's skin, and at the same time defines part of the electrical path (together with the wall of bell 14 and the connector 19) from the terminal of the EKG machine to the patient's skin.

The vacuum bell 14 is particularly adapted to be disposable after one or several uses, and in this regard it will be understood that the bulb 1 may be readily disconnected from bell 14 for use with another bell in a subsequent application.

Figure 3:
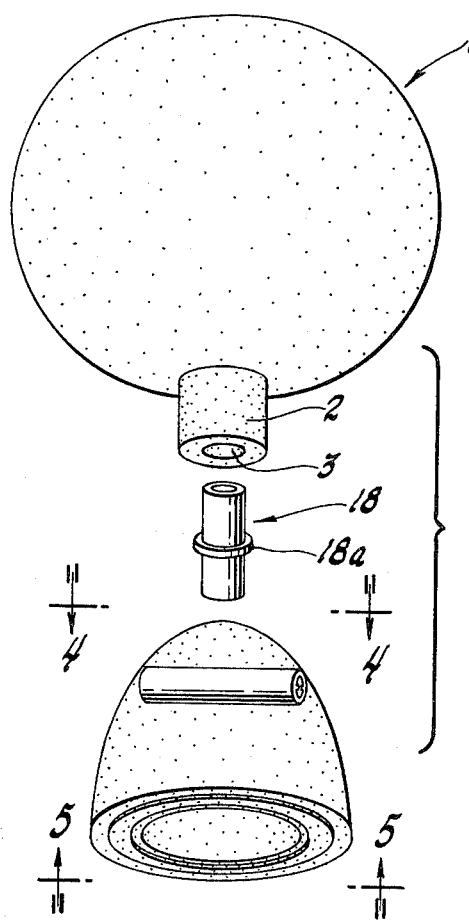
FIG. 3 is a perspective view of a medical electrode apparatus in accordance with a second preferred embodiment of the invention.

With particular reference to FIG. 3, the present invention contemplates that the apparatus may be provided in the form of an electrode kit. Such a kit would include, for example, a plurality of the vacuum bells 14, at least one bulb 1 provided with an insert 18, and a plurality of the annular masses of material 20 positioned respectively in the bells 14. In this regard it will be understood that the masses of material 20 are preferably individually pre-positioned in the concavities 16 of the bells 14, and may be desirably adhesively secured therein.

Although there have been described what are at present considered to be the preferred embodiments of the invention, it will be understood that the invention may be embodied in other specific forms without departing from the spirit or essential characteristics thereof. The present embodiments are therefore to be considered in all respects as illustrative, and not restrictive. The scope of the invention is indicated by the appended claims rather than by the foregoing description.

I claim:

1. A medical instrumentation electrode apparatus, comprising:
    a substantially rigid vacuum bell fabricated of a substantially rigid electrically-conductive material, said vacuum bell having a hollow inner chamber formed therein;
    first means for creating a partial vacuum in said inner chamber of said vacuum bell;
    second means for selectively electrically connecting said vacuum bell to an external medical instrument;
    third means for operably connecting said first means with said vacuum bell such that said first means communicates with said inner chamber of said vacuum bell;
    said inner chamber of said vacuum bell including a lower open end portion defined by a lower peripheral wall portion of said vacuum bell;
    a substantially annular-shaped electrically-conductive member supported by said lower peripheral wall portion, said annular-shaped member providing a secure holding electrical contact with a patient's skin upon evacuation of said vacuum bell by said first means; and
    fourth means for securing said annular-shaped electrically-conductive member to said lower peripheral wall portion in downwardly-depending relation thereto.

2. A medical instrumentation electrode apparatus according to claim 1, wherein:
    said fourth means comprises a substantially annular-shaped concavity formed in said lower peripheral wall portion so as to define an outer concavity surrounding said inner chamber; and said annular-shaped electrically-conductive member comprises a toroidal-shaped mass of electrically-conductive material received within said annular-shaped concavity so as to depend downwardly from said lower peripheral wall portion.

3. A medical instrumentation electrode apparatus according to claim 2, wherein:

said first means comprises a resilient bulb member, said bulb member being provided with a neck;

an upper central portion of said vacuum bell is formed with a through aperture communicating with said inner chamber; and said third means comprises an electrically-conductive substantially tubular shaped insert, the upper portion of said insert being closely received in said neck of said bulb member and the lower portion of said insert being closely received in said through aperture of said vacuum bell.

4. A medical instrumentation electrode apparatus according to claim 2, wherein:

said second means comprises a substantially tubular connector member extending from an outer surface portion of said vacuum bell, said tubular connector member being integrally fabricated from said electrically-conductive material such that said vacuum bell and said tubular connector member comprise a unitary structure; and said electrically-conductive material comprises a substantially rigid electrically-conductive plastic material.

5. A medical instrumentation electrode apparatus according to claim 2, wherein:

said mass of electrically-conductive material received within said annular-shaped concavity comprises an annular mass of electrically-conductive silver-silver chloride gel.

6. A medical instrumentation electrode kit, comprising:

a plurality of substantially rigid vacuum bells fabricated of a substantially rigid electrically-conductive material, each said vacuum bell having an inner chamber formed therein;

at least one first means for creating a partial vacuum in said inner chamber of each said vacuum bell;

a plurality of second means for selectively electrically connecting each said vacuum bell to an external medical instrument;

at least one third means for operably connecting said first means with one of said vacuum bells such that said first means communicates with said inner chamber of said vacuum bell;

said inner chamber of each said vacuum bell including a lower open end portion defined by a lower peripheral wall portion of said vacuum bell, said lower peripheral wall portion having a substantially annular-shaped concavity formed therein so as to define an outer concavity, surrounding said inner chamber; and a plurality of substantially toroidal-shaped electrically-conductive members, each said toroidal-shaped member being receivable in each said outer concavity so as to be supported thereby in downwardly-depending relation to said lower peripheral wall portion of each said vacuum bell.

7. A medical instrumentation electrode kit according to claim 6, wherein:

said second means comprises a substantially tubular connector member extending from an outer surface portion of each said vacuum bell, said tubular connector member being integrally fabricated from said electrically-conductive material such that said vacuum bell and said tubular connector member comprise a unitary structure.

8. A medical instrumentation electrode kit according to claim 6, wherein:

said first means comprises a resilient bulb member, said bulb member being provided with a neck;

an upper central portion of each said vacuum bell is formed with a through aperture communicating with said inner chamber; and said third means comprises an electrically-conductive substantially tubular shaped insert, the upper portion of said insert being adapted to be closely received in said neck of said bulb member and the lower portion of said insert being adapted to be closely received in said through aperture of each said vacuum bell.

9. A medical instrumentation electrode kit according to claim 7, wherein:

said electrically-conductive material comprises a substantially rigid electrically-conductive plastic material.

* * * * *